US006162419A

United States Patent [19]
Perricone et al.

[11] Patent Number: 6,162,419
[45] Date of Patent: *Dec. 19, 2000

[54] STABILIZED ASCORBYL COMPOSITIONS

[75] Inventors: Nicholas V. Perricone, 27 Coginchaug Ct., Guilford, Conn. 06437; Chim Potini, Dekatur, Ill.

[73] Assignee: Nicholas V. Perricone, Guilford, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/756,461

[22] Filed: Nov. 26, 1996

[51] Int. Cl.[7] .................................................... A61K 7/42
[52] U.S. Cl. .............................. 424/59; 514/474; 514/667
[58] Field of Search ..................... 514/474, 667; 424/59

[56] References Cited

U.S. PATENT DOCUMENTS

| | | |
|---|---|---|
| 5,409,693 | 4/1995 | Perricone . |
| 5,545,398 | 8/1996 | Perricone . |
| 5,554,647 | 9/1996 | Perricone ................................ 514/474 |

OTHER PUBLICATIONS

Perricone, N. V., "The Photoprotective and Anti–Inflammatory Effects of Topical Ascorbyl Palmitate", The Journal of Geriatric Dermatology, vol. 1, No. 1, pp. 5–10, 1993.

*Primary Examiner*—Dwayne C. Jones
*Attorney, Agent, or Firm*—St. Onge Steward Johnston & Reens LLC

[57] ABSTRACT

Fatty acid esters of ascorbic acid, particularly saturated fatty acid esters such as ascorbyl palmitate, their salts, ascorbic acid and its salts are solubilized in large amounts, e.g., up to about 25% by weight, and stabilized using special solvent systems. Useful solvents include polyethylene glycol, ethoxydiglycol, propylene glycol, butylene glycol, propylene carbonate, glycerin, a capric glyceride, a caprylic glyceride, an alkyl lactate, an alkyl adipate, an isosorbide, and mixtures thereof. Preferred dermatological compositions made using these solvents with ascorbic acid and/or at least one of its derivatives also include dimethylaminoethanol, tyrosine, proline, cystine, a penetration enhancer such as oleic acid, urea or mixtures thereof, and at least one natural and/or chemical antioxidant. Natural antioxidants that contain at least about 50% polyphenols and 50% catachins such as grape seed or green tea extracts are employed in some embodiments.

20 Claims, No Drawings

STABILIZED ASCORBYL COMPOSITIONS

TECHNICAL FIELD

This invention relates primarily to stabilized compositions of ascorbic acid, ascorbic acid salts, ascorbyl fatty acid esters and/or their salts for dermatological and cosmetic use.

BACKGROUND OF THE INVENTION

Fatty acid esters of ascorbic acid such as ascorbyl palmitate are employed in topical compositions for a variety of purposes such as for treating and/or preventing sunburn (U.S. Pat. No. 5,409,693 to Perricone; this and all other references cited hereafter are hereby expressly incorporated herein by reference in their entireties) and for treating disorders of the skin which are caused by, or are dependent upon, depleted or inadequate collagen levels, and/or oxygen-containing free radicals, and/or oxidative generation of active metabolites via lipoxygenase pathways (U.S. Ser. No. 08/407,413 to Perricone filed Mar. 17, 1995 and allowed Jun. 11, 1996 now U.S. Pat. No. 5,574,063). Topical compositions containing acetylcholine precursors such as dimethylaminoethanol have also been disclosed for the treatment of aging skin and subcutaneous muscles; in some embodiments, the compositions also contain fatty acid esters of ascorbic acid (U.S. Pat. No. 5,554,647 to Perricone).

The compositions are efficacious because a wide variety of skin diseases and skin conditions in which the skin has undergone some form of damage or aging can be traced, either directly or indirectly, to processes which either deplete or inhibit synthesis of collagen, and/or generate oxygen-containing free radicals, and/or oxidatively generate biologically active metabolites, generally via lipoxygenase pathways, which in turn either directly act upon the skin or mediate other processes which have adverse effect on the skin. In radiation-induced skin damage, for example, particularly ultraviolet radiation-induced skin damage (e.g., sunburn), it appears that the transfer of energy from the radiation to the skin results in the generation of excited oxygen species, such as singlet oxygen, the superoxide anion, and hydroxyl radicals, that can damage lipid-rich membranes with the subsequent activation of the chemical mediators of inflammation and/or damage the skin cell membrane and DNA, and also where it appears that the radiation releases arachadonic acid which is then oxidized via two predominant pathways to produce either prostaglandins or leukotrines. Cell membranes are particularly susceptible to attack by free radicals because of their dense molecular structure largely comprising lipids and lipoproteins that are easily oxidized by reactive oxygen species and oxygen-containing free radicals. Where skin is damaged from aging or chronic exposure to sunlight, free radical-induced damage also appears to be involved and collagen content is diminished. In other disease conditions such as psoriasis, a chronic, recurrent, scaling skin disease of unknown etiology, it is possible that hydroxyeicosatetraenoic acids and leukotrines generated by oxidation of arachidonic acid via the lipoxygenase pathway have a role in the pathogenesis of the disease.

Free radical damage to the surface of the skin can be manifested as lines, mottling, discoloration, precancers and cancers. Damage to cell membranes in both epidermis and underlying subcutaneous muscle tissue can result in myriad changes including decrease of cell function, loss of cell permeability, increased intercellular ionic concentration, and decreased cellular capacity to excrete or detoxify waste products. These cause accumulation of waste products in the cells, such as lipofuscin; increase in the potassium content of the cells, which results in their dehydration; and decreased production of messenger RNA and proteins, resulting in decreased cellular repair. Some cells become so dehydrated they cannot function at all. In skin, the regularity of tissue structure is lost, and individual cells enlarge, but the total number of cells decreases approximately 30%. Intercellular collagen and elastin increases. The proportion of soluble collagen decreases, and there may be increased cross-linking between long-chain collagen macromolecules. Elastin loses its discrete structure and elasticity, and exhibits an increased calcium content.

The external appearance of aging individuals is affected not only by changes in the epidermis, but also by subcutaneous changes in underlying muscle tissue. The combination of sagging muscles and aging skin contributes to the overall cosmetic changes typically observed, such as wrinkling, which involves the transition of a formerly smooth skin surface to one that appears unevenly shrunk and/or contracted. When muscles are at rest, a certain amount of tautness usually remains. The residual degree of contraction in skeletal muscles is called muscle tone. In aging individuals, the degree of contraction relaxes, and is particularly obvious in the face. Topical application of acetylcholine precursors such as dimethylaminoethanol helps shorten subcutaneous muscles, resulting in a lift in tissue on the face, chest or other area of application.

Critical to the success of preventing and/or alleviating skin conditions or diseases or collagen deficiencies by topical treatment with fatty acid esters of ascorbic acid and treatment of subcutaneous muscle with acetylcholine precursors such as dimethylaminoethanol is the utilization of the active ingredients which are effective for the purpose without concurrent generation of adverse side effects. Equally important, however, is effective delivery to the sites where active ingredients will act most efficaciously on the disease or condition (or afford protection therefrom). Generally speaking, it is thus necessary for the active ingredients to be deliverable in either an intact form or in a form whereby the active ingredients are exposed or released in the actual environment where their activity is needed. So too, it is of importance that active ingredients be such as to be compatible with a base composition which facilitates topical application and which facilitates application in suitable dosages, and further that the active ingredients either be stable per se or have the ability to be stabilized in admixture with other components, so that preparations can be marketed with a suitably long shelf-life and such that prolonged activity can be obtained once topical application has been made.

In some cases compositions containing fatty acid esters of ascorbic acid cannot be delivered in active form and/or cannot be solubilized in base compositions and/or are unstable at the concentrations required for application and/or color the skin to which they are applied. This is particularly true of compositions containing, for example, high amounts of ascorbyl palmitate (e.g., 20% to 25% by weight), particularly where water must be used as a solvent for some of the ingredients in the formulation. Ascorbic acid is soluble in water, but insoluble in oils, fats, and fat solvents, whereas the converse is true of its fatty acid esters. The differences in solubility make it difficult to prepare compositions containing ascorbic fatty acid esters with water-soluble ingredients, including ascorbic acid. The formulations have a tendency to precipitate on storage.

Moreover, compositions containing ascorbic acid and/or its esters have a tendency to deteriorate on storage, typically by combining with oxygen in the atmosphere and/or in the aqueous solvent to yield inactive forms such as dehydro derivatives. Loss of reducing equivalents is observed, and the compositions yellow and, in extreme cases, brown.

It would be desirable to have stabilized compositions containing ascorbic acid and/or its fatty acid esters of ascorbic acid, particularly high amounts of saturated fatty acid esters.

SUMMARY OF THE INVENTION

It is an object of the invention to provide stable compositions containing ascorbic acid, ascorbic acid salts, ascorbic fatty acid esters, and/or ascorbic fatty acid ester salts.

It is another object of the invention to provide stabilized compositions containing up to about 25% by weight fatty acid esters of ascorbic acid, including compositions that in some embodiments also contain ascorbic acid, that do not change color or precipitate when stored at room temperature for extended periods, and that do not color the skin when used.

It is a further object of the invention to provide compositions containing ascorbic acid and/or fatty acid esters of ascorbic acid that, if formulated to be clear and colorless, remain clear and colorless on storage under the same conditions.

These and other objects are accomplished by the present invention, which provides stabilized ascorbic acid and/or ascorbyl fatty acid ester compositions employing solvent systems that provide greater stability and solubility than that observed in typical water-based systems. The invention correspondingly provides methods for stabilizing ascorbic acid, its fatty acid esters, and their salts and solubilizing ascorbyl fatty acid esters for compositions, particularly compositions containing saturated fatty acid esters such as ascorbyl palmitate and including those also containing ascorbic acid. Typical dermatological and cosmetic compositions of the invention further contain an acetylcholine precursor such as dimethylaminoethanol to enhance subcutaneous muscle tone and tighten the skin. Preferred compositions also contain tyrosine, at least one antioxidant, and a compound that enhances penetration such as oleic acid, urea, and/or mixtures thereof.

Solvent systems of the invention for stabilizing and solubilizing ascorbic acid and/or ascorbic fatty acid esters to form stable compositions include polyethylene glycol, ethoxydiglycol, propylene glycol, butylene glycol, propylene carbonate, glycerin, a capric glyceride, a caprylic glyceride and mixtures thereof, an alkyl lactate, an alkyl adipate, an isosorbide, and mixtures of these. Lauryl lactate, isostearyl lactate and mixtures thereof are used in some embodiments. Alkyl adipates include, but are not limited to, diisopropyl adipate, isocetyl adipate, diisocetyl adipate, dipropyl adipate, and mixtures thereof.

By use of the solvent systems, compositions containing up to about 25% by weight of a saturated fatty acid ester of ascorbic acid such as ascorbyl laurate, ascorbyl myristate, ascorbyl palmitate, ascorbyl stearate, ascorbyl behenate, the corresponding ascorbyl salts such as magesium ascorbyl palmitate or stearate, and mixtures thereof, can be stably prepared in formulations containing water-soluble ingredients such as ascorbic acid and/or ascorbic acid salts, e.g., magnesium ascorbate, calcium ascorbate, sodium ascorbate, and/or potassium ascorbate. Ascorbyl palmitate is used in preferred embodiments.

DETAILED DESCRIPTION OF THE INVENTION

This invention is based upon the development of solvent systems useful for stabilizing and dissolving relatively large concentrations of both ascorbic acid and/or its salts and its fatty acid esters and/or their salts. The invention thus provides for the physical and chemical stability of vitamin C-based compounds in any form.

This invention encompasses methods of solubilizing up to at least about 25% of a fatty acid ester of ascorbic acid and compositions containing the esters thereof. Fatty acid esters of ascorbic acid include ascorbic acid acylated with single or multiple fatty acid groups, wherein the fatty acids typically have 8 to 24 carbon atoms, and their salts. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate, and their salts, e.g., magnesium ascorbyl stearate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate.

This invention further encompasses methods for stabilizing compositions containing ascorbic acid and/or its fatty acid esters and their salts for at least about three months at room temperature, preferably at least about a year, and in some cases two to three years. As used herein, the term "ascorbic acid" includes the free acid, its salts, e.g., calcium ascorbate, magnesium ascorbate, potassium ascorbate, sodium ascorbate, magnesium ascorbyl phosphate, other derivatives, and mixtures thereof. By "stabilizing" is meant maintaining the reducing equivalent of the active ingredient (ascorbic acid or its fatty acid esters) and/or preventing visually apparent color formation for at least about three months, preferably at least about a year, and in some cases for about two to three years.

Typical dermatological compositions of the invention contain from about 1% to about 25% by weight ascorbic fatty acid ester; some embodiments contain higher amounts, e.g., in excess of 50%. As illustrated in the examples that follow, some embodiments are creams that contain only about 2% to about 7% by weight ester such as ascorbyl palmitate. Other compositions such as clear eye gels contain up to about 25%, e.g., from about 20% to about 25%, by weight ascorbyl palmitate. Compositions of the invention include creams, gels, foams, lotions, and other emulsions; some compositions are clear, others are opaque.

In the practice of the invention, fatty acid esters of ascorbic acid are stabilized and solubilized using a solvent selected from the group consisting of polyethylene glycol, ethoxydiglycol, propylene glycol, butylene glycol, propylene carbonate, glycerin, a capric glyceride, a caprylic glyceride, an alkyl lactate, an alkyl adipate, an isosorbide, and mixtures thereof. As used herein, the word "solvent" encompasses both a liquid that dissolves another substance to form a solution as well as a substances that provide homogeneous mixtures and stable suspensions. Polyethylene glycol, ethoxydiglycol, butylene glycol, capric or caprylic glycerides, and alkyl lactates are particularly preferred in some embodiments. Alkyl lactates include, but are not limited to, lauryl lactate, isostearyl lactate, dialkyl lactates and other lactates, including their salts, and mixtures thereof. Alkyl adipates include, but are not limited to, dipropyl adipate, diisopropyl adipate, isocetyl adipate, diisocetyl adipate, their salts, and the like, and mixtures thereof. An example isosorbides is dimethyl isosorbide. Capric and caprylic glycerides include glycerides bearing predominantly capric pendant groups, glycerides bearing predominantly caprylic pendant groups, and those bearing mixtures of capric and caprylic pendant groups, including those that further contain some caproic, pelargonic, and lauric residues such as mixtures derived from lauric oils, and include compositions containing triglycerides as well as compositions containing mixtures of mono-, di- and triglycerides.

Methods of stabilizing and solubilizing ascorbic acid and/or its derivatives and formulations so formed are particularly applicable to the formulation of dermatological compositions and cosmetic compositions. In these applications, compositions that provide an elegant feel are particularly preferred. However, compositions of the invention also encompass soaps and other skin cleansing products, deodorants, talcs, liquid dish washing compositions and other household cleaners and products, particularly those that come in contact with skin when used. Some formulations are useful, however, for hair care products and others for oral hygiene products. In still other embodiments, compositions of the invention are used for nontoxic oral vitamin supplements.

The solvent or solvent mixtures are selected to be conducive to topical application, and ones that form a film or layer on the skin to which the composition is applied so as to localize the application and provide some resistance to washing off by immersion in water or by perspiration and/or one which aids in percutaneous delivery and penetration of the ascorbyl fatty acid ester into lipid layers are particularly preferred. In many embodiments, compositions of the invention contain a penetration enhancer such as oleic acid and/or urea; typical concentrations range from about 0.5% to about 10% by weight. Compositions may also contain acrylate/ceteth copolymers. Example formulations are given hereafter.

To achieve skin tightening and smoothing effects when compositions of the invention are applied to skin, preferred compositions of the invention contain dimethylaminoethanol or other acetylcholine precursors disclosed by Perricone in U.S. Pat. No. 5,554,647. By the term "acetylcholine precursor" is meant any precursor in the biosynthetic pathway of acetylcholine, or related pathways. These include co-factors and precursors of acetylcholine, synthetic enzymes and precursors or enhancers of acetylCoA production. Acetylcholine precursors include, but are not limited to, dimethylaminoethanol, monoaminoethanol, choline, serine, and mixtures thereof. As used herein, "precursors" also include derivatives of precursors such as esters, e.g., acetic acid and para-chlorophenylacetic acid esters of dimethylaminoethanol or monoaminothanol, and the like. Folic acid and vitamin $B_{12}$ augment acetylcholine synthesis in some embodiments. Other embodiments contain choline acetylase agonists and acetylcholinesterase inhibitors to augment acetylcholine synthesis. Dimethylaminoethanol (DMAE) is a preferred precursor. Typical embodiments contain from about 0.1% to about 5% by weight dimethylaminoethanol.

In some embodiments, an effective amount of catecholamines, catecholamine precursors, catecholamine mimics, chemicals that augment the release of catecolamines, or mixtures thereof, are added to the compositions of the invention (as described in U.S. Application Ser. No. 08/525,977 by Perricone, filed Sep. 7, 1995 now U.S. Pat. No. 5,643,586 ). In these embodiments, catecholamine compounds are typically applied in amounts sufficient to increase subcutaneous muscle tone or in amounts to synergestically cooperate with acetylcholine precursors, if present. Catecholamines include epinephrine, norepinephrine, dopa, and serotonin; catecholamine precursors include tyrosine and phenylalanine; and catecholamine mimics include tyramine, ephedrine and amphetamine. Catecholamine precursors are particularly preferred.

Superior compositions are formulated by also incorporating tyrosine into the formulation. It is an advantage of the invention that the solvent systems that solubilize ascorbic fatty acid esters also solublize tyrosine. Compositions containing relatively high amounts of tyrosine, e.g., up to about 10% by weight, for example, feel like silk when applied to the skin. It is an advantage of the invention that compositional incorporation is enhanced by the solvent system of the invention at these high levels.

Preferred compositions of the invention further contain at least one antioxidant. It is an advantage of the invention that ascorbic acid can surprisingly be incorporated into compositions using the special solvent systems described above, though ascorbic acid and ascorbic fatty acid esters are not generally soluble in the same solvents. Other useful antioxidants of the invention include metabisulfites and bisulfites such as sodium metabisulfite or sodium or potassium bisulfite, sulfites, sodium sulfate and other sulfates, polyphenol, natural antioxidants such as glucosoamine glycans, grapeseed extract, proline and cysteine, green tea extract, and catachins typically used in amounts sufficient to stabilize the compositions on storage at room temperature for at least a year and to prevent yellowing.

Some embodiments contain bovine milk proteins (including enzymes) such as γ-lactoglobulin. While not wishing to be bound to any theory, inclusion of these proteins enhances stability of ascorbic acid and/or its derivatives.

Compositions of the invention can further contain α-hydroxy acids such as glycolic and/or lactic acid, at least one additional substance that enhances neurotransmitter synthesis such as pyridoxine, calcium pantothenate, zinc, and mixtures of any of these, and another antioxidant such as vitamin E acetate or linoleate, tocotrienol and other compounds set out in U.S. Pat. No. 5,545,398 to Perricone, or mixtures of any of these. In some embodiments, compositions further contain other ingredients typically observed used in dermatologically acceptable carriers such as emulsifiers, emollients, and, in some instances, thickening agents of natural and synthetic gums.

A typical composition of the invention contains from about 1% to about 25% by weight of a saturated fatty acid ester of ascorbic acid such as ascorbyl laurate, ascorbyl myristate, ascorbyl palmitate, ascorbyl stearate, ascorbyl behenate, and/or mixtures; a solvent selected from the group consisting of polyethylene glycol, ethoxydiglycol, propylene glycol, butylene glycol, propylene carbonate, glycerin, a capric glyceride, a caprylic glyceride, an alkyl lactate, an alkyl adipate, an isosorbide, and mixtures thereof; from about 0.1% to about 5% by weight dimethylaminoethanol; L-tyrosine; a penetration enhancer such as oleic acid and/or urea; and an antioxidant.

Methods for stabilizing ascorbic acid and/or its fatty acid esters and their salts and solubilizing a fatty acid ester of ascorbic acid, particularly saturated esters, in a composition with at least one water-soluble ingredient such as ascorbic acid are correspondingly encompassed by the invention. In the practice of a method of the invention, ascorbic acid and/or an ascorbyl fatty acid ester is dissolved in a solvent selected from the group consisting of polyethylene glycol, ethoxydiglycol, propylene glycol, butylene glycol, propylene carbonate, glycerin, a capric glyceride, a caprylic glyceride, an alkyl lactate, an alkyl adipate, an isosorbide, and mixtures thereof, and adding the dissolved acid and/or ester to a water-based phase.

As set out above, compositions formulated using a method of the invention typically further comprise dimethylaminoethanol, tyrosine, a penetrant, and an antioxidant and optional ingredients described above. These may be added when the oil phase is added to the water phase, or in situ during the emulsification process.

EXAMPLES

The following examples are presented to further illustrate and explain the present invention and should not be taken as limiting in any regard.

EXAMPLE 1

This example illustrates ascorbyl palmitate cream formulations containing 2 to 7% ascorbyl palmitate particularly useful for dermatological and cosmetic purposes.

Various compositions were prepared by blending the following ingredients:

|  | Original Formula | Formula With Metabisulfite |
|---|---|---|
| D.I. Water | 55.10 | 58.10 |
| Sodium Hyaluronate | 17.00 | 10.00 |
| Urea | 5.00 | 5.00 |
| L-Tyrosine | 5.00 | 5.00 |
| Miglycol ® 8810 | 4.00 | 4.00 |
| DC 345 Fluid | 3.00 | 3.00 |
| Hydrolyzed Glycosoamineglycons | 3.00 | 3.00 |
| Ascorbyl palmitate | 2.00 | 5.00 |
| DMAE | 2.00 | 1.00 |
| Zinc Sulfate USP | 1.00 | 1.00 |
| Polysorbate-20 | 0.60 | 0.60 |
| Xanthan Gum | 0.50 | 0.50 |
| Vitamin B$_6$ HCl, USP | 0.50 | 0.50 |
| Pantethiene | 0.50 | 0.50 |
| Imidaxolidinyl Urea | 0.60 | 0.50 |
| Oxynex ® K | 0.20 | 0.20 |
| Sodium Metabisulfite | — | 2.00 |
| Titanium Dioxide | — | 0.10 |

The formula with metabisulfite was slick and dried slowly.

Other formulations were prepared from ingredients as follows:

5% Ascorbyl Palmitate Formulation # 1

% WW

| Ingredient | Formula | Formula |
|---|---|---|
| Purified water | Q.S. to 100.00 | Q.S to 100.00 |
| Ascorbyl palmitate | 5.00 | 5.00 |
| L-Tyrosine | 5.00 | 5.00 |
| Urea | 3.50 | 3.50 |
| Propyleneglycol | 3.00 | 3.00 |
| Glycerylmonostearate | 3.00 | 3.00 |
| MyristylMyristate | 2.00 | 2.00 |
| DMAE | 1.00 | 2.00 |
| PEG-20 Stearate | 1.50 | 1.50 |
| Oleic Acid | 0.60 | 0.60 |
| Zinc Sulfate | 0.50 | 0.50 |
| Germaben ® 11E | 0.50 | 0.50 |
| Rhodogel | 0.20 | 0.30 |
| Vitamin B$_6$.HCl | 0.20 | 0.20 |
| EDTA-Na$_2$ | 0.20 | 0.20 |
| Vitamin E linoleate | 0.20 | 0.20 |
| Titanium Dioxide | 0.20 | 0.20 |
| Pentithiene | 0.10 | 0.10 |

5% Ascorbyl Palmitate Formulation # 2

| | % W/W |
|---|---|
| Purified Water | Q.S to 100.00 |
| Octyldodecanol | 13.00 |
| Cetearyl Ester wax | 6.00 |
| Cetearyl Alcohol | 6.00 |
| Ascorbyl Palmitate | 5.00 |
| L-Tyrosine | 5.00 |
| Urea | 3.50 |
| Sorbitanmonostearate | 2.50 |
| Polysorbate-60 | 2.50 |
| Glycerin-USP | 2.00 |
| Benzyl Alcohol | 1.00 |
| Olei Acid | 0.60 |
| Zinc Sulfate | 0.50 |
| Germaben ® 11 E | 0.50 |
| Vitaniin E Acetate | 0.25 |
| Titanium Dioxide | 0.25 |
| Vitamin B$_6$ HCl | 0.20 |
| DMAE | 0.20 |
| Pentithiene | 0.10 |
| EDTA-Na$_2$ | 0.10 |

5% Ascorbyl Palmitate Formulation # 3

| | % W/W |
|---|---|
| Purified Water | QS to 100.00 |
| Ascorbyl Palmitate | 5.00 |
| L-Tyrosine | 5.00 |
| Urea | 3.50 |
| Propyleneglycol | 3.00 |
| Glyceryl Monostearate-pure | 3.00 |
| Myristyl Myristate | 2.00 |
| DMAE | 2.00 |
| PEG-20 Stearate | 1.50 |
| Oleic Acid | 0.60 |
| Zinc Sulfate | 0.50 |
| Pentithiene | 0.50 |
| Germaben ® 11E | 0.50 |
| Xanthan Gum | 0.40 |
| Titanium Dioxide | 0.30 |
| EDTA-Na$_2$ | 0.25 |
| Vitamin B$_6$ HCl | 0.20 |
| Vitamin E Linoleate | 0.20 |

A 5% ascorbyl palmitate cream containing glycolic acid was also prepared.

| Ingredient | % w/w |
|---|---|
| Purified Water | QS to 100.00 |
| Xanthan Gum | 0.25 |
| Propyleneglycol | 3.00 |
| Urea | 3.50 |
| Zinc Sulfate | 0.50 |
| EDTA-Na$_2$ | 0.25 |
| Pentethiene | 0.10 |
| Vitamin B HCl | 0.20 |
| Glycolic Acid | 0.20 |
| Oleic Acid | 0.60 |
| GMS-pure | 3.00 |
| PEG-20 Stearate | 1.50 |
| Myristyl Myristate | 2.00 |
| Ascorbyl Palmitate | 5.00 |
| Vitamin E Linoleate | 0.20 |
| L-Tyrosine | 5.00 |

-continued

| Ingredient | | % w/w |
|---|---|---|
| | Germaben ® llE | 0.50 |
| | DMAE | 1.00 |
| | Titanium Dioxide | 0.30 |

A 7% cream was also prepared. The following phases were made as follows:

| Ingredient | | % w/w |
|---|---|---|
| I | D.I.Water | 54.30 |
| | Carbomer Ultrez 10 | 0.60 |
| | Sodium Hyaluronate | 0.50 |
| | Hydrolyzed glycosoamineglucans | 0.50 |
| | Urea | 3.00 |
| | Zinc Sulfate | 1.00 |
| | Vitamin $B_6$ HCl | 0.50 |
| | Pentethine | 0.50 |
| II | Cetiol A | 6.50 |
| | D/C Fluid 200-50 cst | 4.00 |
| | Schercemol 185 | 3.50 |
| | DIC Fluid 345 | 3.50 |
| | Stearic Acid | 2.00 |
| | Cetearyl Alcohol | 0.75 |
| | Sorbitanmonostearate | 1.50 |
| | C12–18 Alkyl Bster | 0.75 |
| | Polysorbate-20 | 0.50 |
| | Tocopherol Acetate | 0.50 |
| III | Phenonip | 1.20 |
| | Parabens ® -Methyl, Propyl | 0.30 |
| | Genrmal ® 115 | 0.08 |
| | Germal ® II | 0.08 |
| | DMAE | 2.00 |
| IV | Sodium Metabisulfite | 2.00 |
| | Water | 3.00 |
| V | Ascorbyl Palmitate | 7.00 |
| | L-Tyrosine | 3.00 |
| VI | Gotu Kola ® Extract | 0.64 |
| VI | Fragrance BBA # 961697 | 0.60 |

To prepare the cream, phase I was heated to 75° C., and phase II, to 70° C. Phase I was placed in a Homo-mixer, and Phase II added with the mixer on and mixed until a very good emulsion had been formed. The emulsion was cooled to 65° C. Phase III, IV, V were then added and mixed well with the mixer. The formulation was cooled to 55° C. and put under a sweeping agitation mixer. The mixer was turned off, and Phase VI and VII, added after it reached a temperature of 40° C. When the temperatuer reached 35° C., the cream was packaged.

A 7% ascorbyl plamitate cream was also prepared. The following phases were formulated:

| Ingredient | | % w/w |
|---|---|---|
| I | D.I. Water | 54.30 |
| | Sodium Hyaluronate | 10.00 |
| | Urea | 5.00 |
| | Hydrolyzed Glycosoamineglucans | 1.00 |
| | Zinc Sulfate | 1.00 |
| | Vitamin $B_6$ HCl | 0.50 |
| | Pentethine | 0.50 |
| II | Miglyol 8810 | 4.00 |
| | D/C Fluid 345 | 3.00 |
| | Tocopherol Acetate | 0.50 |
| III | DMAE | 2.00 |
| | Germaben IIE | 0.60 |

-continued

| Ingredient | | % w/w |
|---|---|---|
| IV | Sodium Metabisulfite | 2.00 |
| | Water | 3.00 |
| V | L-Tyrosine | 5.00 |
| | Ascorbyl Palmitate | 7.00 |
| VI | Fragrance BBA# 961697 | 0.60 |

To prepare the cream, Phase I was heated to 75° C. and Phase II was heated to 70° C. Phase II was then added to I in a Homo-mixer turned on to full speed. When the emulsion temperature reached 65° C., Phase III, IV and V were added (with the Homo-mixer kept on). The remaining batch was put under a sweeping mixer when it reached 50° C., and mixing was continued. Fragrance was added when the temperature reached 40° C., and the cream was packaged.

An eye cream containing 7% ascorbyl pelmitate was also prepared. The following phases were formulated:

| Ingredient | | % w/w |
|---|---|---|
| I | D.I.Water | 50.00 |
| | Carbomer Ultrez 10 | 0.60 |
| | Sod.Hyaluronate | 0.50 |
| | Hydrolyzed glycosoamineglucans | 0.50 |
| | Urea | 3.00 |
| | Zinc Sulfate | 1.00 |
| | Vitamin $B_6$ HCl | 0.50 |
| | Pentethine | 0.50 |
| II | Cetiol A | 6.50 |
| | D/C Fluid 200-50 cst | 4.00 |
| | Schercemol ® 185 | 3.50 |
| | DIC Fluid 345 | 3.50 |
| | Stearic Acid | 2.00 |
| | Cetearyl Alcohol | 0.75 |
| | Sorbitanmonostearate | 1.50 |
| | $C_{12-18}$ Alkyl Ester | 0.75 |
| | Polysorbate-20 | 0.50 |
| | Tocopherol Acetate | 0.50 |
| III | Phenonip ® | 1.20 |
| | Parabens ®Methyl, Propyl | 0.30 |
| | Germal ® 115 | 0.08 |
| | Germal ® II | 0.08 |
| | DMAE | 2.00 |
| IV | Sodium Metabisulfite | 2.00 |
| | Water | 3.00 |
| V | Ascorbyl Palmitate | 7.00 |
| | L-Tyrosine | 3.00 |
| VI | Gotu Kola ® Extract | 0.50 |
| | Gentella ® Extract | 1.00 |
| VI | Fragrance BBA # 961697 | 0.60 |

Phase I was heated to 75° C., and Phase II, to 70° C. Phase II was added to I in a Homo-mixer turned on, and mixed well until a very good emulsion had been formed. This was cooled down to 65° C., and Phase III, IV and V were added and mix well 65° C. well with the Homo-mixer on. This was cooled to 55° C. and put under a sweeping agitation mixer. The Homo-mixer was turned off, and Phase VI and VII, added after the mixture reached a temperature of 40° C. The cream was packaged when the temperature reached 35° C.

EXAMPLE 2

Two lip-plumper formulations containing 5% ascorbyl palmitate are prepared in this example.

| Ingredient | HNC 118-86 | HNC 118-107 |
|---|---|---|
| Purified Water | QS to 100.00 | QS to 100.00 |
| Rhodigel | 0.20 | 0.25 |
| Propyleneglycol | 3.00 | 3.50 |
| Urea | 3.50 | 1.00 |
| Zinc Sulfate | 0.50 | — |
| EDTA-$Na_2$ | 0.25 | 0.20 |
| Pentethiene | 0.10 | — |
| Vitamin B HCl | 0.20 | 0.50 |
| Oleic Acid | 0.60 | 0.60 |
| GMS-pure | 3.00 | 3.00 |
| PEG-20 Stearate | 1.50 | 1.50 |
| Myristyl Myristate | 2.00 | 2.00 |
| Ascorbyl palmitate | 5.00 | 5.00 |
| Vit. E Linoleate | 0.20 | 0.20 |
| Cetyl Alcohol | — | 0.50 |
| Tyramine HCl | 1.00 | 1.00 |
| Germaben llE | 0.50 | 0.50 |
| DMAE | 1.00 | — |
| Titanium Dioxide | 0.30 | 0.30 |

EXAMPLE 3

This example illustrates foam cleansers prepared with 3% ascorbyl palmitate.

The following proportions of ingredients were employed in one composition:

| Ingredient | % w/w |
|---|---|
| Purified Water | q.s to 100.00 |
| Sodium Lauryl Sulfate | 10.00 |
| Lauryl Polyglucose | 4.00 |
| Lauramide DEA | 4.00 |
| Cocamidopropyl Betaine | 2.00 |
| Ascorbyl Palmitate | 3.00 |
| Polysorbate-20 | 1.00 |
| Sodium Chloride | 0.55 |
| Germaben ® llE | 0.55 |
| DMAE | 0.50 |
| Citric Acid | 0.45 |
| Pamello ® # 7713 (flavor) | 0.20 |

Ascorbyl palmitate was dissolved in lauramide DEA and polysorbate-20 by heating to 65° C. and then cooling to room temperature to form a pre-mix. Sodium lauryl sulfate, lauryl glucose, and betaine were added to water and mixed until dissolved. The ascorbyl palmitate pre-mix was then added to the water solution. The mixture was cooled to 25° C. and the remaining ingredients were added. The final pH varied between 5.5 and 6.5.

Another preparation contained differences in salt, sodium lauryl sulfate, citric acid, DMAE and EDTA:

| Ingredient | % w/w |
|---|---|
| Purified Water | QS to 100.00 |
| Ammonium Lauryl Sulfate (29%) | 34.50 |
| Lauryl Polyglucose | 4.00 |
| Lauramide DEA | 4.00 |
| Cocamidopropyl Betaine | 2.00 |
| Ascorbyl Palmitate | 3.00 |
| Polysorbate-20 | 1.00 |
| Sodium Chloride | 0.45 |
| Germaben ® llE | 0.50 |
| DMAE | 0.25 |
| Citric Acid | 0.50 |
| Pamello ® # 7713 | 0.20 |
| EDTA-Disodium | 0.20 |

The pH of a 10% solution was 5.98.

EXAMPLE 4

Clear eye gels containing 20 to 25 % ascorbyl palmitate are prepared in this example. The compositions are particularly useful for application to the area around the eyes.

20% Clear Eye-Gel # 1

| Ingredient | % w/w |
|---|---|
| Diethyleneglycol Monoethylether | 79.30 |
| Ascorbyl Palmitate | 20.00 |
| DMAE | 0.20 |
| 200 vis. Ethylcellulose | 0.50 |

Ascorbyl palmitate was predissolved in DEME and heated to 45° C. and form a cyrstal-clear phase which was then cooled to room temperature. DMAE was added, and the mixture was put on a premier mill. Cellulose gum was added, and the resulting mixture was mixed well until all the gum goes into solution.

20.00% Clear Eve Gel # 2

Another formulation was prepared by mixing:

| Ingredient | % w/w |
|---|---|
| Ethoxydiglycol | QS to 100.00 |
| Ascorbyl Palmitate | 20.00 |
| DMAE | 0.20 |
| Silica | 2.50 |

20.00% Clear Eve Gel # 3

| Ingredient | % w/w |
|---|---|
| Ethoxydiglycol | QS to 100.00 |
| Ascorbyl Palmitate | 20.00 |
| DMAE | 0.20 |
| Ethylcellulose | 0.50 |

A 25% clear eye gel was prepared by mixing

| Ingredient | % w/w |
|---|---|
| Ethoxydiglycol | QS to 100.00 |
| Ascorbyl Palmitate | 25.00 |
| DMAE | 0.20 |
| Coenzyme Q10 | 0.25 |

A 1% solution of the last formulation had a pH of 6.9.

EXAMPLE 5

This example compares and contrasts compositions containing 0.25% DMAE and 1% to 20% ascorbyl palmitate prepared as described above with compositions containing ascorbic acid.

|  | Ascorbyl Palmitate (%) | Ascorbic Acid (%) |
|---|---|---|
|  | 1.00 | 0.40 |
|  | 5.00 | 2.10 |
|  | 10.00 | 4.30 |
|  | 15.00 | 6.40 |
|  | 20.00 | 8.50 |
| Oxidation sensitivity | Slow | Fast |
| Light Sensitivity | Slow | Fast |
| Water Solubility | No | High |
| Degradation | Negligible | Very High |
| Hydrolysis | Negligible | Very High |

It can be seen that use of ascorbyl palmitable results in more stable compositions at all levels than that achieved using ascorbic acid.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for stabilizing and solubilizing an ascorbic acid compound selected from the group consisting of a fatty acid ester of ascorbic acid, a salt of a fatty acid ester of ascorbic acid, and mixtures thereof, in a composition with at least one water-soluble ingredient comprising dissolving, homogeneously mixing, or stably dispersing the ascorbyl fatty acid ester or salt in a solvent selected from the group consisting of polyethylene glycol, ethoxydiglycol, propylene glycol, butylene glycol, propylene carbonate, glycerin, a capric glyceride, a caprylic glyceride, an alkyl lactate, an alkyl adipate, an isosorbide, and mixtures thereof, and adding the dissolved, homogenously mixed, or stably dispersed solvent phase containing the ascorbic acid compound to an aqueous phase containing the water-soluble ingredient.

2. A method according to claim 1 wherein the solvent is selected from the group consisting of polyethylene glycol, ethoxydiglycol, butylene glycol, a capric glyceride, a caprylic glyceride, an alkyl lactate, and mixtures thereof.

3. A method according to claim 1 wherein the composition further comprises tyrosine and a penetrant selected from the group consisting of oleic acid, urea, and mixtures thereof.

4. A method according to claim 1 wherein the fatty acid ester of ascorbic acid is ascorbyl palmitate.

5. A method according to claim 1 wherein a water-soluble ingredient is ascorbic acid or an ascorbic acid salt.

6. A method according to claim 1 wherein the solvent is selected from the group consisting of polyethylene glycol, ethoxydiglycol, butylene glycol, a capric glyceride, a caprylic glyceride, an alkyl lactate, and mixtures thereof.

7. A method for stabilizing an ascorbic acid composition containing a saturated $C_8$ to $C_{24}$ fatty acid ester or fatty acid ester salt of ascorbic acid in concentrations of between about 1% to about 50% by weight, and at least one water-soluble ingredient comprising dissolving, homogenously mixing, or stably dispersing the ascorbic acid ester, the ascorbic acid ester salt, or mixtures thereof, in a solvent selected from the group consisting of polyethylene glycol, ethoxydiglycol, propylene glycol, butylene glycol, propylene carbonate, glycerin, a capric glyceride, a caprylic glyceride, an alkyl lactate, an alkyl adipate, an isosorbide, and mixtures thereof, and then homogenizing the dissolved or dispersed ester with an aqueous phase containing the water-soluble ingredient.

8. A method according to claim 7 wherein the solvent is selected from the group consisting of polyethylene glycol, ethoxydiglycol, and butylene glycol.

9. A method according to claim 7 wherein the alkyl lactate is selected from the group consisting of lauryl lactate, isostearyl lactate, and mixtures thereof, and the alkyl adipate is selected from the group consisting of diisopropyl adipate, isocetyl adipate, diisocetyl adipate, dipropyl adipate, and mixtures thereof.

10. A method according to claim 7 wherein the water-soluble ingredient is ascorbic acid.

11. A method according to claim 7 wherein the water-soluble ingredient is tyrosine.

12. A method according to claim 7 wherein the ascorbic fatty acid ester is ascorbyl palmitate.

13. A method according to claim 7 wherein the concentration of ascorbic acid ester in the final composition is from about 2% to about 7% by weight.

14. A method according to claim 7 wherein the concentration of ascorbic acid ester in the final composition is from about 20% to about 25% by weight.

15. A method of preparing a composition containing from about 20% to about 50% of a fatty acid ester of ascorbic acid selected from the group consisting of ascorbyl laurate, ascorbyl myristate, ascorbyl palmitate, ascorbyl stearate, ascorbyl behenate, and mixtures thereof, and at least one water-soluble ingredient comprising dissolving, homogenously mixing or stably dispersing the fatty acid ester in a solvent selected from the group consisting of polyethylene glycol, ethoxydiglycol, butylene glycol, propylene carbonate, a capric glyceride, a caprylic glyceride, an isosorbide, an alkyl lactate, and mixtures thereof, and then homogenizing the dissolved ester with an aqueous phase containing the water-soluble ingredient such that the composition is stabilized from precipitation or color change when stored at room temperature for at least about three months.

16. A method according to claim 15 wherein the fatty acid ester is ascorbyl palmitate.

17. A method according to claim 16 which contains from about 20% to about 25% ascorbyl palmitate.

18. A method according to claim 15 wherein the solvent is selected from the group consisting of polyethylene glycol, ethoxydiglycol, dimethyl isosorbide, and butylene glycol.

19. A method according to claim 15 wherein the alkyl lactate is selected from the group consisting of lauryl lactate, isostearyl lactate, and mixtures thereof, and the alkyl adipate is selected from the group consisting of diisopropyl adipate, isocetyl adipate, diisocetyl adipate, dipropyl adipate, and mixtures thereof.

20. A method according to claim 15 wherein the water-soluble ingredient is ascorbic acid or tyrosine.

* * * * *